United States Patent [19]

Green et al.

[11] 4,444,790

[45] Apr. 24, 1984

[54] QUATERNARY AMMONIUM DISINFECTANTS

[75] Inventors: Harold A. Green, Havertown, Pa.; Alfonso N. Petrocci, Glen Rock; Zdzislaw W. Dudzinski, Clifton, both of N.J.

[73] Assignee: Millmaster Onyx Group, Inc., New York, N.Y.

[21] Appl. No.: 411,380

[22] Filed: Aug. 25, 1982

Related U.S. Application Data

[63] Continuation-in-part of Ser. No. 382,399, May 27, 1982.

[51] Int. Cl.³ .................... C07C 87/30; A01N 33/12
[52] U.S. Cl. .................................. 424/329; 564/291; 424/316; 260/501.15
[58] Field of Search ................ 564/291; 424/329, 316; 260/501.15

[56] References Cited

U.S. PATENT DOCUMENTS

| | | | |
|---|---|---|---|
| 3,054,678 | 9/1962 | Michener et al. | 424/329 |
| 3,535,380 | 10/1970 | Dudzinski et al. | 424/329 |
| 3,754,033 | 8/1973 | Shay et al. | 564/291 |
| 3,819,656 | 6/1974 | Barie et al. | 564/291 |
| 3,836,669 | 9/1974 | Dadekian | 424/329 |
| 3,880,613 | 4/1975 | Oswald et al. | 424/329 |
| 4,073,888 | 2/1978 | Snyder | 424/329 |
| 4,165,375 | 8/1979 | Berger | 424/329 |

*Primary Examiner*—James H. Reamer
*Attorney, Agent, or Firm*—Arthur A. Jacobs

[57] ABSTRACT

Decyl dimethylquaternaryammonium salts utilizable as disinfectants in the presence of hard water or organic soil, the term "decyl" referring to a mixture of branched primary branched chain alkyl groups having 10 carbon atoms.

23 Claims, No Drawings

QUATERNARY AMMONIUM DISINFECTANTS

This application is a continuation-in-part of application Ser. No. 382,399, filed May 27, 1982.

STATEMENT OF PRIOR ART

U.S. Pat. No. 3,733,420
U.S. Pat. No. 3,754,033
U.S. Pat. No. 3,836,669

As disclosed in application Ser. No. 382,399, quaternary ammonium salts in which either one or two of the substituents bonded to the quaternary nitrogen is a decyl radical comprising a mixture of primary 10-carbon atom branched chains were found to be very effective anti-microbial agents.

However, it is well known in the art that most biocidal quaternary ammonium compounds lose a considerable amount of their anti-microbial activity in the presence of hard water or organic soil, although certain heretofore known dialkyl dimethylammonium salts retain enough activity in the presence of these contaminants to be useful as bacteriostatic agents or sanitizers, but are inferior disinfectants. (A "sanitizer" is defined herein as a compound which reduces the concentration of microorganisms to a predetermined acceptable level without necessarily killing 100% of the organisms. A "disinfectant" is defined herein as a compound which kills 100% of the organisms).

The effectiveness of quaternary ammonium compounds as sanitizers in hard water is usually measured by the "Germicidal and Detergent Sanitizers Test" AOAC, 13th edition, page 61, (whereby increasing concentrations of hardness are used in order to determine the maximum water hardness—ordinarily in terms of ppm. as calcium carbonate) in which a concentration of a predetermined amount of a quaternary will kill 99.999% of the test organisms in the inoculum after 30 seconds of contact. This test is also often referred to as the "Hard Water Tolerance Test".

The "Germicidal and Detergent Sanitizers Test" may be adequate when the microbial contaminants involve only the less virulant, non-pathological species of microorganisms, or when the intent is merely to reduce the microbial content to predetermined acceptable levels. But when virulent, pathological species of microorganisms are the contaminants, then mere sanitization is insufficient. In such a case, only disinfection (100% kill of microorganisms) is tolerable.

The effectiveness of quaternaries as disinfectants is usually measured by the "Use Dilution Test" (AOAC, 13th edition, page 58). This test measures the minimum concentration of a disinfectant which will kill 100% of the microorganisms on a hard surface in 10 minutes.

Although the "Use Dilution Test" often serves as a means for comparing the effectiveness of quaternaries as disinfectants, it has a serious practical shortcoming; namely, it is performed in distilled water. Most communities in the United States, and probably in the world, are in hard water areas, and since hard water reduces the anti-microbial effectiveness of disinfectants, it is necessary to modify the AOAC "Use Dilution Test" so that it will take water hardness into consideration.

In order to determine the actual effectiveness of quaternary disinfectants in hard water, certain aspects of the "Use Dilution Test" have here been combined with some aspects of the "Germicidal and Detergent Sanitizers Test". In such combined test a concentration of disinfectant is selected and, using that concentration, successive "Use Dilution Tests" are performed at increasing stepwise concentrations of hard water contaminant until the quaternary fails to kill 100% of the test organisms. The maximum hard water level at which the quaternary passes this test is the significant measure of disinfectant effectiveness in hard water.

Since quaternary ammonium compounds are often used for cold sterilization, or chemical sterilization of hard surfaces, it is an object of this invention to provide disinfectants which are effective on hard surfaces, both in the presence of hard water as a diluent and in the presence of organic soil.

It is, in addition, an object of this invention to provide quaternary ammonium compounds which are superior disinfectants relative to the best of the known prior quaternaries, especially in the presence of hard water or organic soil.

Other objects will become apparent from the following specification and claims.

In accordance with the present invention, it has now been discovered that decyl-n-decyl dimethylammonium salts (wherein the term "decyl", as used throughout this specification, connotes a mixture of primary 10-carbon atom branched chains, as distinguished from the term "n-decyl", which connotes the normal decyl radical) are highly effective disinfectant agents in the presence of either hard water, organic soil, or both.

In addition to the discovery of the effectiveness of decyl-n-decyl dimethylammonium salts as disinfectants in hard water or organic soil, it has also been found that although both di-n-decyl and di-decyl dimethylammonium salts are relatively poor disinfectants, by themselves, in hard water or in the presence or organic soil, when combined, they exert a synergistic effect on each other whereby the mixture also becomes an effective disinfectant both in hard water and in the presence of organic soil.

The "decyl" group of this invention is derived from commercial decyl alcohol, such as is previously produced by Exxon Chemical Co. and United States Steel Co. It has a CAS number of 68441-08-6* and is essentially a mixture of branched primary alcohols in which the longest straight chain has at least two branches, the preponderant component being trimethlheptanol.

The decyl-n-decyl dimethylammonium salts, as well as the di-decyl and di-n-decyl dimethylammonium salts, are prepared by the methods described fully in the aforementioned parent application Ser. No. 382,339. The steps of the synthesis are well known, as indicated in the aforesaid parent application.

In order to illustrate the present invention, the following quaternary compounds, each of which is represented by the names of the two alkyl substitutents followed by "DMAC", as an abbreviation for dimethylammonium chloride, were prepared:

decyl-n-decyl DMAC
di-decyl DMAC
di-n-decyl DMAC

In addition to the above single compounds, the following mixtures were also prepared:

90% by weight of di-decyl DMAC, 10% of weight of di-n-decyl DMAC
50% by weight of di-decyl DMAC, 50% by weight of di-n-decyl DMAC
10% by weight of di-decyl DMAC, 90% by weight of di-n-decyl DMAC 25% by weight of di-decyl DMAC, 25% by weight of di-n-decyl DMAC and 50% by weight of decyl-n-decyl DMAC.

All of the above seven materials were subjected to the AOAC "Use Dilution Test", in distilled water, against Psuedomonas aeruginosa, in order to determine the minimum concentration at which each would kill 100% of the microorganisms. Each passed the "Use Dilution Test" at the minimum concentration of 500 ppm in distilled water.

These same seven materials, each in the aforesaid concentration of 500 ppm, were then subjected to a modified form of the "Use Dilution Test", using the techniques of the "Germicidal and Detergent Sanitizers Test", whereby, in the presence of 5% blood serum as organic contaminant, the concentration of hardness was increased in steps of 50 ppm in separate experiments until the level of water hardness was reached in which the disinfectant failed to kill 100% of the organisms. This test is clearly the best method for testing the hard water performance of disinfectants.

The results of the tests, wherein all concentrations were verified by replicate tests, are shown in the following table:

| Concentration of Hardness in Water (In ppm of Hardness) Against Psuedomonas aerugenosa ATCC #15442, Using 500 ppm of Quaternary | | |
|---|---|---|
| | Passed | Failed |
| di-n-decyl DMAC | 250 | 300 |
| di-decyl DMAC | 250 | 300 |
| decyl-n-decyl DMAC | 550 | 600 |
| 90% di-decyl DMAC<br>10% di-n-decyl DMAC | 450 | 500 |
| 50% di-decyl DMAC<br>50% di-n-decyl DMAC | 500 | 550 |
| 10% di-decyl DMAC<br>90% di-n-decyl DMAC | 500 | 550 |
| 25% di-decyl DMAC<br>25% di-n-decyl DMAC<br>50% decyl-n-decyl DMAC | 550 | 600 |

In distilled water, di-decyl DMAC, di-n-decyl DMAC and decyl-n-decyl DMAC all have approximately the same disinfectant effectiveness.

The results shown in the above table clearly indicate the following:

1. In the presence of hard water and organic soil, decyl-n-decyl dimethylammonium chloride, by itself is, the most effective hard water disinfectant because it can tolerate a greater concentration of hard water and organic soil than the other quaternaries by themselves.

2. When used in admixtures with each other, di-n-decyl and di-decyl dimethylammonium chlorides, although showing relatively poor effectiveness by themselves in hard water and organic soil, potentiate each other to greatly increase the effectiveness of the mixture under such conditions, and the effectiveness of this mixture is further enhanced by the additon of decyl-n-decyl dimethylammonium chloride.

The invention claimed is:

1. A quaternary ammonium compound having the structural formula:

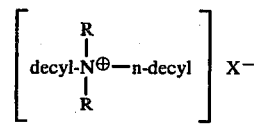

wherein R is a lower alkyl group of from 1 to 4 carbon atoms and X is either a halogen having an atomic weight greater than 30, methosulfate or ethosulfate, the term "decyl" referring to a mixture of primary branched chain alkyl groups each of which has 10 carbon atoms and consists of a straight chain having at least two branches and the term "n-decyl" referring to the normal decyl group.

2. The compound of claim 1 wherein X is chlorine.
3. The compound of claim 1 wherein R is $CH_3$.
4. The compound of claim 1 wherein X is chlorine and R is $CH_3$.
5. A disinfectant composition comprising an aqueous solution of a quaternary ammonium compound having the structural formula:

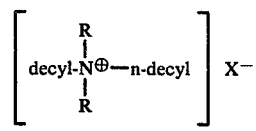

wherein R is a lower alkyl group of from 1 to 4 carbon atoms and X is either a halogen having an atomic weight greater than 30, methosulfate or ethosulfate, the term "decyl" referring to a mixture of primary branched chain alkyl groups each of which has 10 carbon atoms and consists of a straight chain having at least two branches and the term "n-decyl" referring to the normal decyl group, said quaternary ammonium compound being present in said solution in an amount of at least 500 ppm.

6. The composition of claim 5 wherein X is chlorine.
7. The composition of claim 5 wherein R is $CH_3$.
8. The composition of claim 5 wherein X is chlorine and R is $CH_3$.
9. The composition of claim 5 wherein said solution contains at least about 400 ppm of hardness as measured in terms of ppm of calcium carbonate.
10. A method of disinfection which comprises applying to undesired bacteria a disinfectingly effective amount of a quaternary ammonium compound having the structural formula:

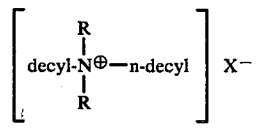

wherein R is a lower alkyl group of from 1 to 4 carbon atoms and X is either a halogen having an atomic weight greater than 30, methosulfate or ethosulfate, the term "decyl" referring to a mixture of primary branched chain alkyl groups each of which has 10 carbon atoms and consists of a straight chain having at least two branches and the term "n-decyl" referring to the normal decyl group.

11. The method of claim 10 wherein X is chlorine.

12. The method of claim 10 wherein R is $CH_3$.

13. The method of claim 10 wherein X is chlorine and R is $CH_3$.

14. The method of claim 10 wherein said quaternary ammonium compound is in an aqueous solution in an amount of at least about 500 ppm.

15. The method of claim 10 wherein said solution contains at least about 400 ppm of hardness as measured in terms of ppm of calcium carbonate.

16. The method of claim 10 wherein said quaternary ammonium compound is applied to bacteria on a hard surface.

17. The method of claim 10 wherein said quaternary ammonium compound is in admixture with di-decyl dimethylammonium halide and di-n-decyl dimethylammonium halide, the term "decyl" as used in "di-decyl" referring to a mixture of primary branched chain alkyl groups having 10 carbon atoms and the term "di-n-decyl" referring to the normal decyl group.

18. The method of claim 17 wherein said quaternary ammonium compound comprises about 50% by weight of the active ingredients of the mixture.

19. A disinfectant composition comprising an aqueous solution of a quaternary ammonium compound wherein the quaternary ammonium compound is present in an amount of at least 500 ppm, said quaternary ammonium compound being selected from the group consisting of (a) decyl-n-decyl dimethylammonium halide, (b) a mixture of di-decyl dimethylammonium halide and di-n-decyl-dimethylammonium halide, and (c) a mixture of di-decyl dimethylammonium halide, di-n-decyl dimethylammonium halide and decyl-n-decyl dimethylammonium haldide, the term "decyl" referring to a mixture of branched chain alkyl groups each of which has 10 carbon atoms and consists of a straight chain having at least two branches and the term "n-decyl" referring to the normal decyl group.

20. The composition of claim 19 wherein the solution contains at least 400 ppm of hardness as measured in terms of calcium carbonate.

21. The composition of claim 19 wherein the mixture of di-decyl and di-n-decyl dimethylammonium halides contains at least about 10% by weight of the di-n-decyl halide.

22. The composition of claim 19 whereas the mixture of di-decyl, di-n-decyl and decyl-n-decyl dimethylammonium halides contains about 50% of the decyl-n-decyl halide, the remainder being formed of about equal amounts of the other two halides.

23. The composition of claim 19 wherein the halides are chlorides.

* * * * *